US012605271B2

(12) United States Patent
Stead

(10) Patent No.: US 12,605,271 B2
(45) Date of Patent: Apr. 21, 2026

(54) EXTERNAL URINARY CATHETERIZATION DEVICE AND METHOD OF USE

(71) Applicant: Roxanna Stead, Canyon Lake, CA (US)

(72) Inventor: Roxanna Stead, Canyon Lake, CA (US)

( * ) Notice: Subject to any disclaimer, the term of this patent is extended or adjusted under 35 U.S.C. 154(b) by 707 days.

(21) Appl. No.: 18/086,825

(22) Filed: Dec. 22, 2022

(65) Prior Publication Data

US 2024/0207084 A1     Jun. 27, 2024

(51) Int. Cl.
A61F 5/455      (2006.01)
A61F 5/451      (2006.01)
A61G 9/00      (2006.01)

(52) U.S. Cl.
CPC ............... *A61F 5/455* (2013.01); *A61G 9/006* (2013.01); *A61F 5/451* (2013.01)

(58) Field of Classification Search
CPC ........ A61F 5/4404; A61F 5/451; A61F 5/455; A61G 9/006
See application file for complete search history.

(56) References Cited

U.S. PATENT DOCUMENTS

| | | | |
|---|---|---|---|
| 4,246,901 A | 1/1981 | Michaud | |
| 5,074,855 A | 12/1991 | Rosenbluth | |
| 5,678,564 A | 10/1997 | Lawrence | |
| 9,629,756 B2 | 4/2017 | Zilm | |

| | | | |
|---|---|---|---|
| 10,226,375 B2 | 3/2019 | Kinkade | |
| 12,220,520 B2 * | 2/2025 | Radl | A61M 1/743 |
| 12,274,638 B2 * | 4/2025 | Spector | A61F 5/4405 |
| 2003/0195484 A1 * | 10/2003 | Harvie | A61F 5/455 |
| | | | 604/355 |
| 2004/0176731 A1 * | 9/2004 | Cheng | A61F 5/455 |
| | | | 604/329 |
| 2013/0317467 A1 | 11/2013 | Campbell | |
| 2017/0266031 A1 * | 9/2017 | Sanchez | A61F 5/443 |
| 2020/0000646 A1 | 1/2020 | Lee | |
| 2020/0046544 A1 * | 2/2020 | Godinez | A61F 5/455 |
| 2021/0186744 A1 * | 6/2021 | Spector | A61F 5/455 |
| 2021/0228795 A1 * | 7/2021 | Hughett | A61F 5/451 |
| 2022/0280711 A1 * | 9/2022 | Radl | A61M 1/743 |
| 2022/0287689 A1 * | 9/2022 | Johannes | A61F 5/453 |
| 2023/0099821 A1 * | 3/2023 | Radl | A61M 1/742 |
| | | | 604/321 |

(Continued)

FOREIGN PATENT DOCUMENTS

CA           967265           5/2015

*Primary Examiner* — Guy K Townsend

(57)           ABSTRACT

An external urinary catheterization device for externally catheterizing a female includes a shell, which defines an interior space and which is substantially impermeable to urine. A cutout is positioned in an upper face of the shell. The shell is positionable between legs of a female with the cutout over her a vulva. A fill material, which is positioned in and which substantially occupies the interior space, wicks urine from the vulva into the interior space. A tube, which is attached to and which extends from the shell, is in fluidic communication with the interior space and is operationally engageable to tubing that extends from, and which is operationally engaged to, a vacuum assembly. The tube allows for passage of the urine from the fill material so that the urine is suctioned through the tubing and into a reservoir of the vacuum assembly.

11 Claims, 6 Drawing Sheets

(56)      References Cited

U.S. PATENT DOCUMENTS

| | | | | |
|---|---|---|---|---|
| 2023/0138269 A1* | 5/2023 | Abdelal | ................. | A61F 5/451 604/347 |
| 2024/0099874 A1* | 3/2024 | Sanchez | ................. | A61F 5/453 |
| 2024/0108491 A1* | 4/2024 | Newton | ................. | A61F 5/455 |
| 2024/0180737 A1* | 6/2024 | Newton | ............... | A61F 5/4404 |
| 2024/0207084 A1* | 6/2024 | Stead | .................... | A61G 9/006 |
| 2024/0341999 A1* | 10/2024 | Godinez | ............. | A61B 10/007 |

* cited by examiner

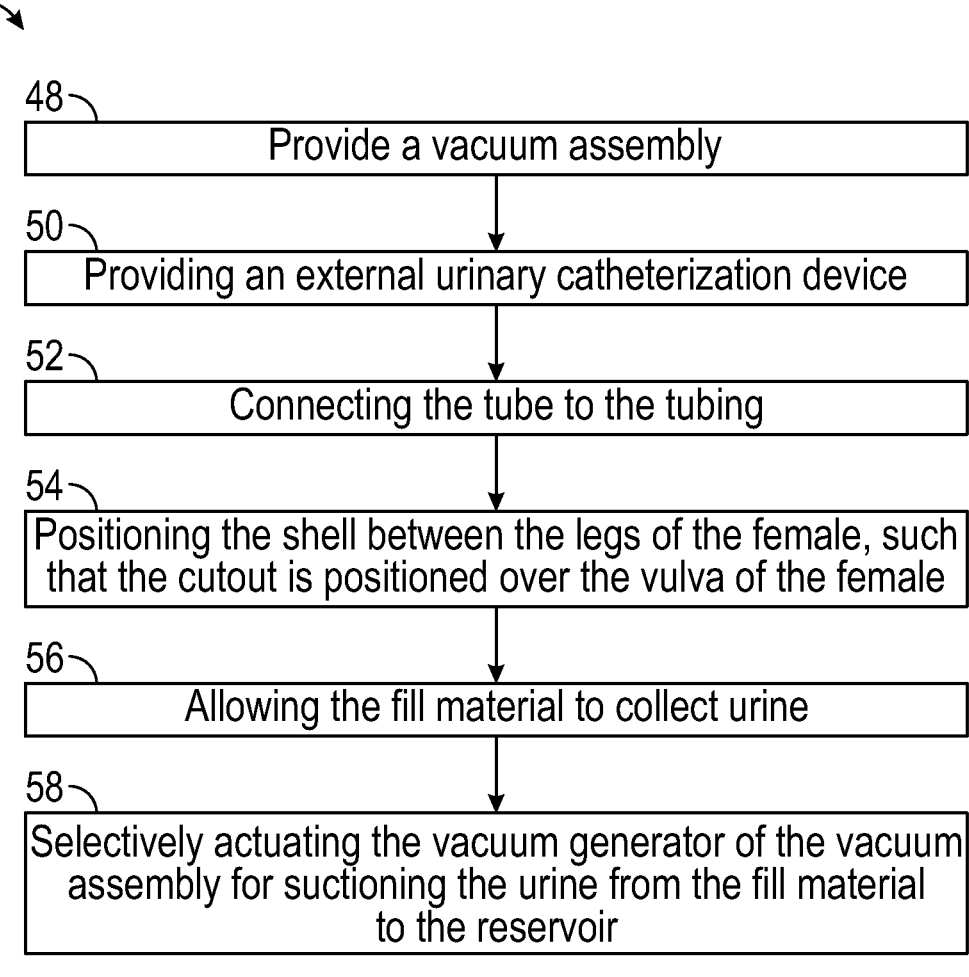

46

48
Provide a vacuum assembly

50
Providing an external urinary catheterization device

52
Connecting the tube to the tubing

54
Positioning the shell between the legs of the female, such that the cutout is positioned over the vulva of the female 56
Allowing the fill material to collect urine 58
Selectively actuating the vacuum generator of the vacuum assembly for suctioning the urine from the fill material to the reservoir

FIG. 9

EXTERNAL URINARY CATHETERIZATION DEVICE AND METHOD OF USE

(b) CROSS-REFERENCE TO RELATED APPLICATIONS

Not Applicable

(c) STATEMENT REGARDING FEDERALLY SPONSORED RESEARCH OR DEVELOPMENT

Not Applicable

(d) THE NAMES OF THE PARTIES TO A JOINT RESEARCH AGREEMENT

Not Applicable

(e) INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

(f) STATEMENT REGARDING PRIOR DISCLOSURES BY THE INVENTOR OR JOINT INVENTOR

Not Applicable

(g) BACKGROUND OF THE INVENTION

(1) Field of the Invention

The disclosure relates to catheterization devices and more particularly pertains to a new catheterization device for externally catheterizing a female. The present invention discloses a catheterization device for a female comprising a shell that can be positioned comfortably over the vulva so that urine collects in a fill material and then can be suctioned off to a reservoir of a vacuum assembly

(2) Description of Related Art Including Information Disclosed Under 37 CFR 1.97 and 1.98

The prior art relates to catheterization devices, which may comprise at least one element that is inserted vaginally to help in retaining the device in place. Other prior art catheterization devices comprise a ring like structure that is sealably positioned around the urinary meatus of a female or a cup like structure sealably positioned around the vulva of the female. What is lacking in the prior art is a catheterization device for a female that can be positioned comfortably over the vulva and which comprises a shell that collects urine in a fill material, with the urine then being suctioned off to a reservoir of a vacuum assembly.

(h) BRIEF SUMMARY OF THE INVENTION

An embodiment of the disclosure meets the needs presented above by generally comprising a shell, which defines an interior space and which is substantially impermeable to urine. A cutout is positioned in an upper face of the shell. The shell is configured to be positionable between legs of a female such that the cutout is positioned over a vulva of the female. A fill material, which is positioned in and which substantially occupies the interior space, is configured to wick urine. The fill material thus is configured to wick urine from the vulva into the interior space. A tube, which is attached to and which extends from the shell, is in fluidic communication with the interior space and is configured to be operationally engaged to tubing that extends from, and which is operationally engaged to, a vacuum assembly. The tube is configured to allow for passage of the urine from the fill material so that the urine is suctioned through the tubing and into a reservoir of the vacuum assembly.

Another embodiment of the disclosure includes an external urinary catheterization system, which comprises an external urinary catheterization device, as described in the disclosure above, and a vacuum assembly. The tubing of the vacuum assembly is operationally engaged to the tube of the external urinary catheterization device. The tube is configured to allow for passage of the urine from the fill material so that the urine is suctioned through the tubing and into the reservoir.

Yet another embodiment of the disclosure includes a method for externally catheterizing a female comprises first and second provision steps, which entail providing a vacuum assembly and an external urinary catheterization device, respectively, as described in the disclosure above. A setup step of the method is connecting the tube to the tubing. Operational steps of the method are positioning the shell between the legs of the female, allowing the fill material to collect urine, and selectively actuating the vacuum assembly for suctioning the urine from the fill material to the reservoir.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

(i) BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 9 is a flow diagram for a method utilizing an embodiment of the disclosure.

(j) DETAILED DESCRIPTION OF THE INVENTION

Figure 1:
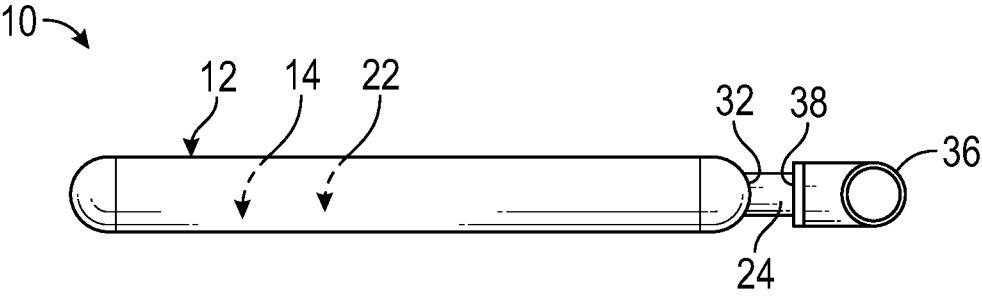
FIG. 1 is a side view of an external urinary catheterization device according to an embodiment of the disclosure.
Figure 2:
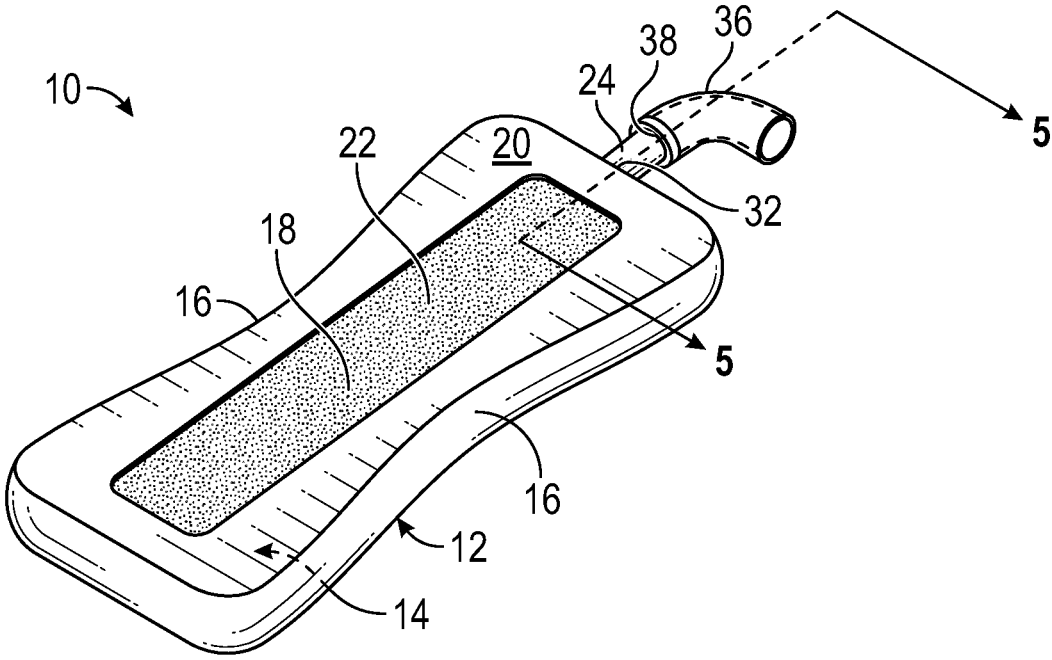
FIG. 2 is an isometric perspective view of an embodiment of the disclosure.

With reference now to the drawings, and in particular to FIGS. 1 through 9 thereof, a new catheterization device embodying the principles and concepts of an embodiment of the disclosure and generally designated by the reference numeral 10 will be described.

Figure 3:
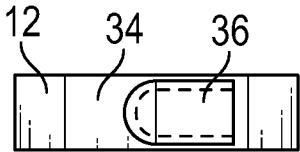
FIG. 3 is an end view of an embodiment of the disclosure.
Figure 4:
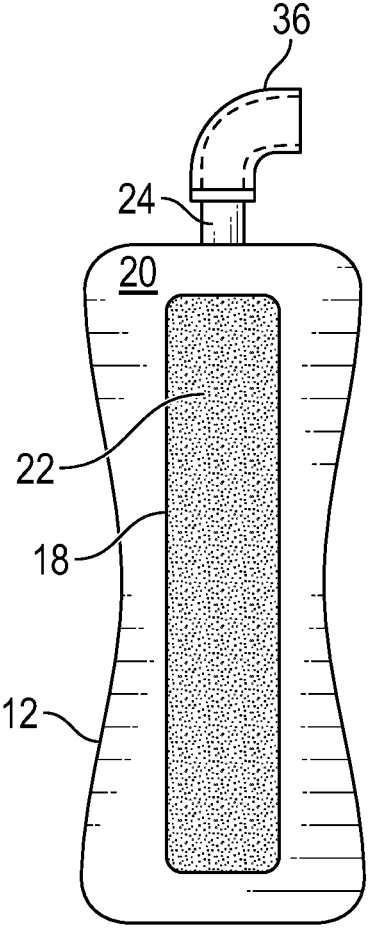
FIG. 4 is a top view of an embodiment of the disclosure.
Figure 5:
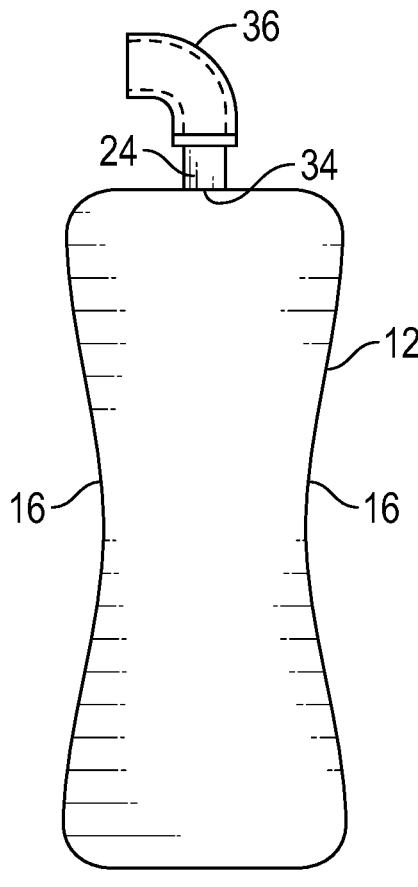
FIG. 5 is a bottom view of an embodiment of the disclosure.

As best illustrated in FIGS. 1 through 9, the external urinary catheterization device 10 generally comprises a shell 12, which defines an interior space 14 and which comprises rubber, silicone, elastomer, or the like, so that the shell 12 is substantially impermeable to urine. Opposed sides 16 of the shell 12 are concavely arcuate, as shown in FIG. 3, so that the shell 12 complements contours between legs of a female. A cutout 18 is positioned in an upper face 20 of the shell 12. The shell 12 is configured to be positionable between the legs of the female such that the cutout 18 is positioned over a vulva of the female.

A fill material 22, which comprises one or more of meshed wool, cotton, polyester, polyethylene, and microfiber cloth, is positioned in and substantially occupies the interior space 14. The fill material 22 thus is configured to wick urine from the vulva into the interior space 14. The present invention also anticipates the cutout 18 being mesh covered with a nonabsorbent material to limit direct contact of the fill material 22 with the vulva.

A tube 24, which is attached to and which extends from the shell 12, is in fluidic communication with the interior space 14 and is configured to be operationally engaged to tubing 26 that extends from, and which is operationally engaged to, a vacuum assembly 28. The tube 24 is configured to allow for passage of the urine from the fill material 22 so that the urine is suctioned through the tubing 26 and into a reservoir 30 of the vacuum assembly 28. The present invention is anticipated to be useful for patients in hospitals and nursing homes who are female and incontinent. The external urinary catheterization device 10 also is anticipated to be useful to females in home care settings.

Figure 6:
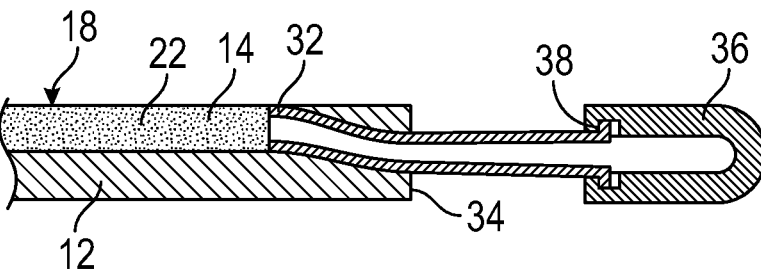
FIG. 6 is a cross-sectional view of an embodiment of the disclosure.
Figure 7:
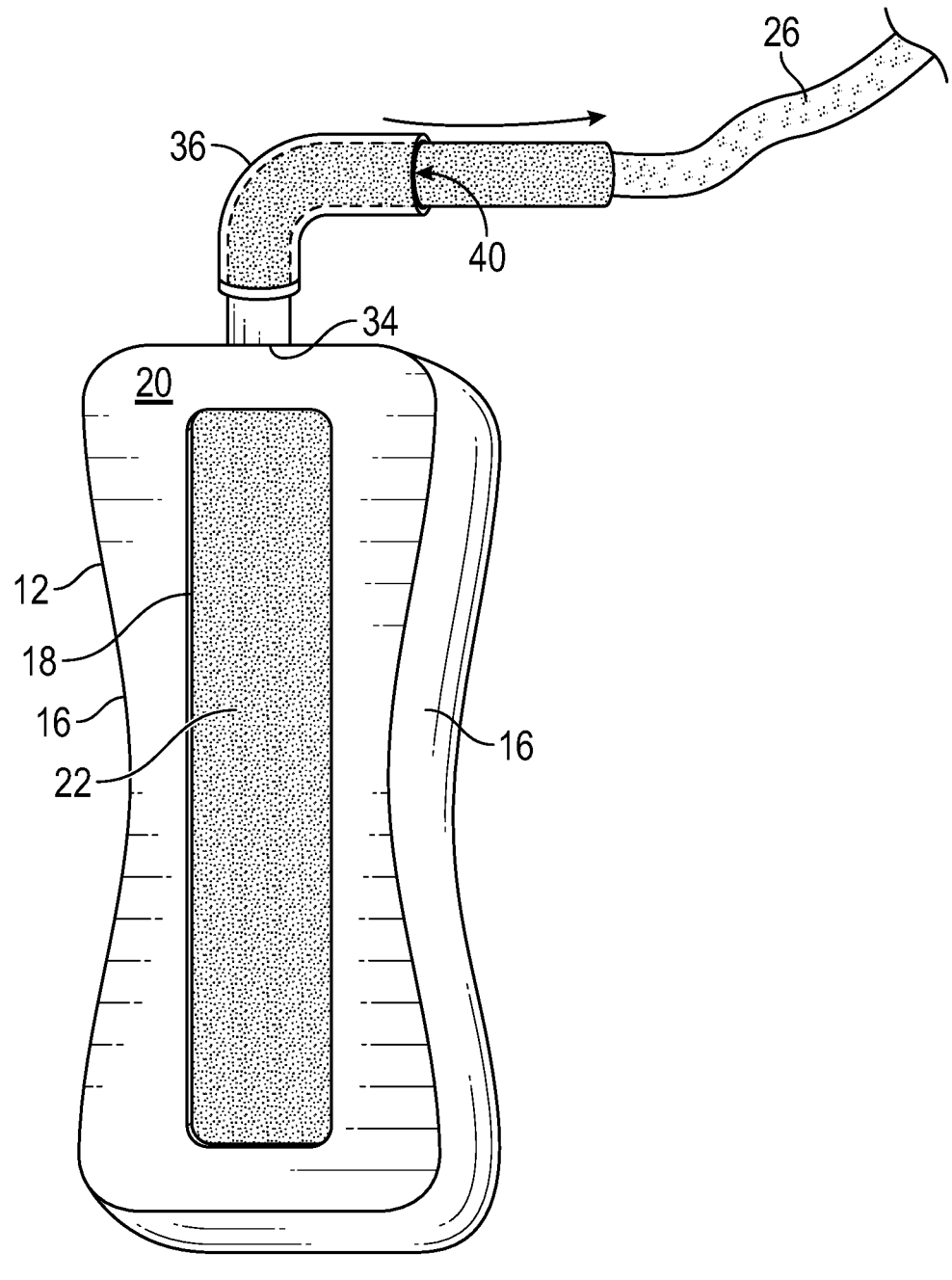
FIG. 7 is an in-use view of an embodiment of the disclosure.

As shown in FIG. 6, a first terminus 32 of the tube 24 extends from a respective opposed end 34 of the shell 12. An elbow connector 36 is rotationally attached to a second terminus 38 of the tube 24 and is configured for insertion of a distal end 40 of the tubing 26 so that the tube 24 is in fluidic communication with the vacuum assembly 28. The elbow connector 36 being rotatable relative to the tube 24, and thus rotatable relative to the shell 12, helps to keep the shell 12 in place over the vulva when the female turns or otherwise moves in a bed. Additionally, the tubing 26 extending from the elbow connector 36 to the reservoir 30 can be positioned more easily to render the external urinary catheterization device 10 and the tubing 26 less noticeable, thereby increasing privacy for the female who is externally catheterized.

Figure 8:
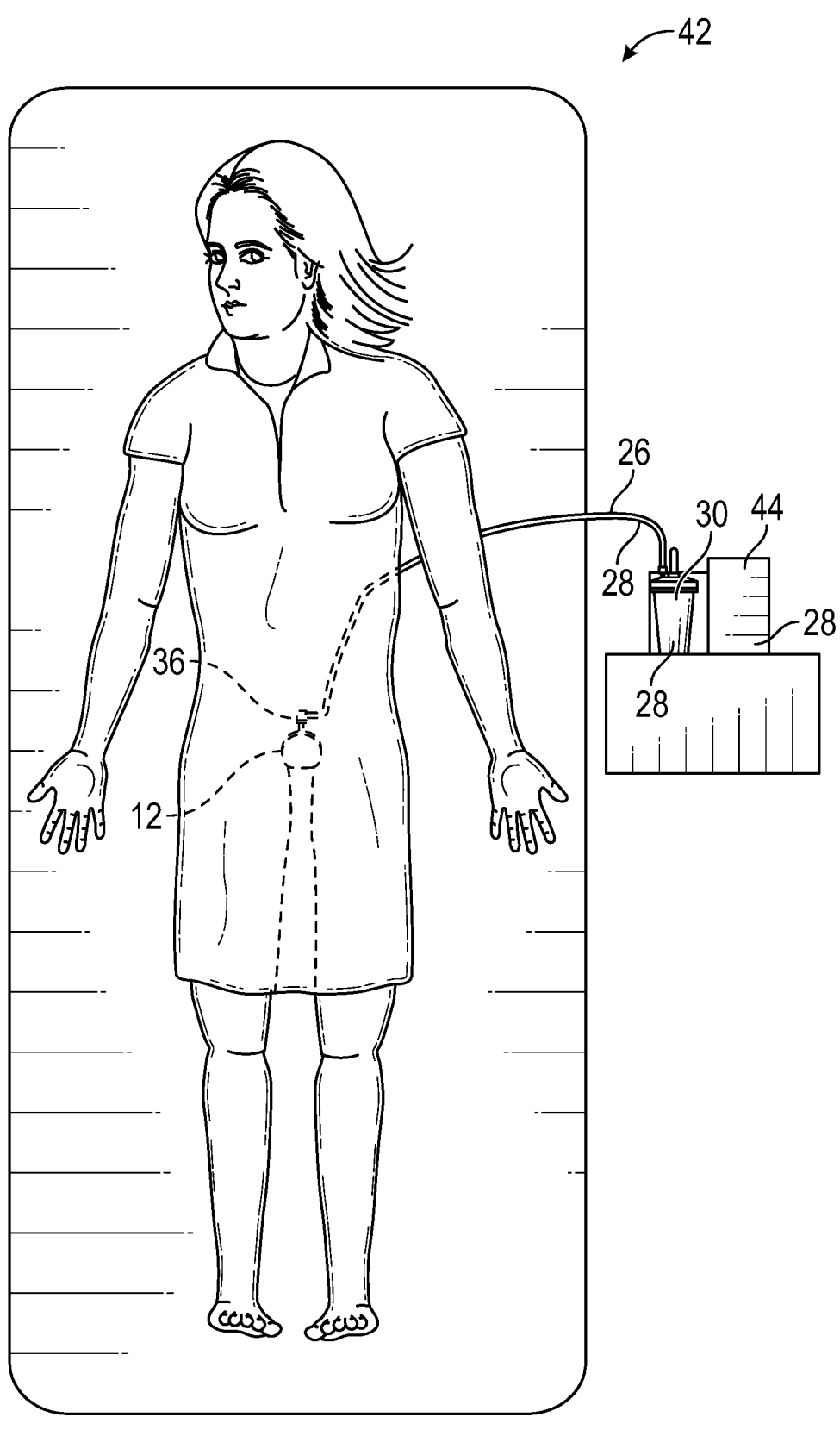
FIG. 8 is an in-use view of an embodiment of the disclosure.

The present invention anticipates an external urinary catheterization system 42, as shown in FIG. 8. The external urinary catheterization system 42 comprises an external urinary catheterization device 10, as described in the specification above, and a vacuum assembly 28. The vacuum assembly 28 comprises a reservoir 30 that is operationally engaged to and in fluidic communication with a vacuum generator 44. Tubing 26 extends from and is operationally engaged to the reservoir 30. The tubing 26 also is operationally engaged to the tube 24 of the external urinary catheterization device 10. The tube 24 thus is configured to allow for passage of the urine from the fill material 22 so that the urine is suctioned through the tubing 26 and into the reservoir 30.

In use, the external urinary catheterization device enables a method for externally catheterizing a female 46, which comprises a first provision step 48 that entails providing a vacuum assembly 28. A second provision step 50 of the method 46 is providing an external urinary catheterization device 10, as described in the specification above. A setup step 52 of the method 46 is connecting the tube 24 to the tubing 26. A first operational step 54 of the method 46 is positioning the shell 12 between the legs of the female so that the cutout 18 is positioned over the vulva of the female. A second operational step 56 of the method 46 is allowing the fill material 22 to collect urine. A third operational step 58 of the method 46 is selectively actuating the vacuum generator 44 of the vacuum assembly 28 to suction the urine from the fill material 22 to the reservoir 30.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An external urinary catheterization device comprising:
   a shell defining an interior space, the shell being substantially impermeable to urine, the shell being elongated between opposed ends of the shell, said shell having an upper face and a lower face, the upper face having concave lateral sides between the opposed ends of the shell;
   a cutout positioned in the upper face of the shell, wherein the shell is configured for positioning between legs of a female such that the cutout is positioned over a vulva of the female;
   a fill material positioned in and substantially occupying the interior space, the fill material being configured for wicking urine, wherein the fill material is configured for wicking urine from the vulva into the interior space; and
   a tube attached to and extending from the shell, such that the tube is in fluidic communication with the interior space, the tube being configured for operationally engaging tubing extending from and operationally engaged to a vacuum assembly, wherein the tube is configured passage of the urine from the fill material, such that the urine is suctioned through the tubing and into a reservoir of the vacuum assembly.

2. The external urinary catheterization device of claim 1, wherein opposed sides of the shell are concavely arcuate, such that the shell complements contours between the legs of the female.

3. The external urinary catheterization device of claim 1, wherein the shell comprises rubber, silicone, or elastomer.

4. The external urinary catheterization device of claim 1, wherein the fill material comprises one or more of meshed wool, cotton, polyester, polyethylene, and microfiber cloth.

5. The external urinary catheterization device of claim 1, further including:

a first terminus of the tube extending from a respective opposed end of the shell; and an elbow connector rotationally attached to a second terminus of the tube, the elbow connector being configured for insertion of a distal end of the tubing, such that the tube is in fluidic communication with the vacuum assembly.

6. An external urinary catheterization system comprising:

a vacuum assembly comprising:

a vacuum generator, a reservoir operationally engaged to and in fluidic communication with the vacuum generator, and tubing extending from and operationally engaged to the reservoir;

a shell defining an interior space, the shell being substantially impermeable to urine, the shell being elongated between opposed ends of the shell, said shell having an upper face and a lower face, the upper face having concave lateral sides between the opposed ends of the shell;

a cutout positioned in the upper face of the shell, wherein the shell is configured for positioning between legs of a female such that the cutout is positioned over a vulva of the female;

a fill material positioned in and substantially occupying the interior space, the fill material being configured for wicking urine, wherein the fill material is configured for wicking urine from the vulva into the interior space; and a tube attached to and extending from the shell, such that the tube is in fluidic communication with the interior space, the tube being operationally engaged to the tubing, wherein the tube is configured passage of the urine from the fill material, such that the urine is suctioned through the tubing and into the reservoir.

7. The external urinary catheterization system of 6, wherein opposed sides of the shell are concavely arcuate, such that the shell complements contours between the legs of the female.

8. The external urinary catheterization system of 6, wherein the shell comprises rubber, silicone, or elastomer.

9. The external urinary catheterization system of 6, wherein the fill material comprises one or more of meshed wool, cotton, polyester, polyethylene, and microfiber cloth.

10. The external urinary catheterization system of 6, further including:

a first terminus of the tube extending from a respective opposed end of the shell;

an elbow connector rotationally attached to a second terminus of the tube; and a distal end of the tubing being inserted into the elbow connector, such that the tube is in fluidic communication with the vacuum assembly.

11. A method for externally catheterizing a female comprising the steps of:

providing a vacuum assembly comprising:

a vacuum generator, a reservoir operationally engaged to and in fluidic communication with the vacuum generator, and tubing extending from and operationally engaged to the reservoir;

providing an external urinary catheterization device comprising:

a shell defining an interior space, the shell being substantially impermeable to urine, the shell being elongated between opposed ends of the shell, said shell having an upper face and a lower face, the upper face having concave lateral sides between the opposed ends of the shell, a cutout positioned in the upper face of the shell, wherein the shell is configured for positioning between legs of a female such that the cutout is positioned over a vulva of the female, a fill material positioned in and substantially occupying the interior space, the fill material being configured for wicking urine, and a tube attached to and extending from the shell, such that the tube is in fluidic communication with the interior space, the tube being configured for engaging the tubing;

connecting the tube to the tubing;

positioning the shell between the legs of the female, such that the cutout is positioned over the vulva of the female;

allowing the fill material to collect urine; and selectively actuating the vacuum generator of the vacuum assembly for suctioning the urine from the fill material to the reservoir.

* * * * *